US00PP22162P2

(12) United States Plant Patent
Burton

(10) Patent No.: US PP22,162 P2
(45) Date of Patent: Sep. 27, 2011

(54) ***BESCHORNERIA* PLANT NAMED 'BESYS'**

(50) Latin Name: *Beschorneria yuccoides*
Varietal Denomination: BESYS

(75) Inventor: Graeme John Burton, Ohaupo (NZ)

(73) Assignee: Lifetech Laboratories Ltd, Auckland (NZ)

( * ) Notice: Subject to any disclaimer, the term of this patent is extended or adjusted under 35 U.S.C. 154(b) by 0 days.

(21) Appl. No.: 12/798,182

(22) Filed: Mar. 31, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Susan McCormick Ewoldt
(74) *Attorney, Agent, or Firm* — Mark P. Bourgeois

(57) ABSTRACT

A new cultivar of *Beschorneria* plant named 'BESYS' that is characterized by variegated leaves having a center yellow stripe with dark green margins.

1 Drawing Sheet

Botanical classification: *Beschorneria yuccoides.*
Variety denomination: 'BESYS'.

BACKGROUND OF THE INVENTION

The present invention relates to a new and distinct cultivar of *Beschorneria* plant botanically known as *Beschorneria yuccoides* and hereinafter referred to by the cultivar name 'BESYS'.

'BESYS' is a naturally occurring whole plant mutation of an unnamed *Beschorneria yuccoides* plant (not patented). 'BESYS' was discovered in a greenhouse in a cultivated area of Hamilton, New Zealand in 2005.

Asexual reproduction first occurred by tissue culture in 2006 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Beschorneria* cultivar 'BESYS'. These traits in combination distinguish 'BESYS' as a new and distinct cultivar apart from other existing known varieties of *Beschorneria.*

1. *Beschorneria* 'BESYS' exhibits variegated leaves having a center yellow stripe with dark green margins.

The closest comparison cultivar is the unnamed parent *Beschorneria* plant. The new cultivar 'BESYS' is distinguishable from the unnamed parent plant by the following characteristics:

1. 'BESYS' exhibits leaves having a center yellow stripe with dark green margins that extend along the full length of the leaf. The leaves of the unnamed parent plant are solid green.

'BESYS' can be compared to typical plants of the *Beschorneria* species. The new cultivar 'BESYS' is distinguishable from typical plants of the *Beschorneria* species by the following characteristics:

1. 'BESYS' exhibits leaves that have a center yellow stripe with dark green margins. The leaves of typical plants of the *Beschorneria* species are all green.

BRIEF DESCRIPTION OF THE DRAWING

The accompanying photograph illustrates the distinguishing traits of *Beschorneria* 'BESYS'. The plant in the photograph shows an overall view of a 3 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Beschorneria* cultivar named 'BESYS'. Data was collected in Hamilton, New Zealand from 3 year old outdoor grown plants. The time of year was summer in the Southern Hemisphere. The temperature range during the day was 14 to 20° Centigrade and 4 to 10° Centigrade at night. Color determinations are in accordance with The Royal Horticultural Society Colour Chart 1995 edition, except where general color terms of ordinary dictionary significance are used. The growing requirements are similar to the species. 'BESYS' has not been tested under all possible conditions and phenotypic differences may be observed with variations in environmental, climatic, and cultural conditions, however, without any variance in genotype.

Botanical classification: *Beschorneria yuccoides* 'BESYS'.
Annual or perennial: Perennial succulent.
Parentage: 'BESYS' is a naturally occurring whole plant mutation of an unnamed *Beschorneria yuccoides* cultivar.
Vigor: Moderate.
Growth habit: Clumping.
Height: 120 cm. in height.
Width: 120 cm. in width.
Low temperature tolerance: −4 degrees Centigrade.
High temperature tolerance: 30 degrees Centigrade.
Propagation: Tissue culture.
Time to produce a rooted cutting or liner (summer): 3 months.
Time to produce a rooted cutting or liner (winter): 4 months.
Crop time: Approximately 3 years.
Root: Medium thickness, fleshy.
Stem:
*Branching habit.*—Basal.
*Stem color.*—201A.

Foliage:

*Leaf arrangement.*—Rosette.

*Compound or single.*—Single.

*Quantity of leaves per plant.*—Average 42.

*Leaf shape.*—Linear.

*Leaf apex.*—Acuminate.

*Leaf base.*—Truncate.

*Leaf length.*—80 cm. in length.

*Leaf width.*—11 cm. in width.

*Texture.*—Both sides glabrous.

*Pubescence.*—Absent.

*Venation.*—Absent.

*Spines.*—Absent.

*Leaf margin.*—Entire.

*Young leaf color* (*lower surface*).—Yellow center stripe 1C at base fades to 2B at tip, stripe is 2 cm. wide at middle tapering towards tips with margins 135A.

*Young leaf color* (*upper surface*).—Yellow center stripe 11B, stripe is 1.5 cm. wide at middle tapering towards tips with margins 135A.

*Mature leaf color* (*lower surface*).—Yellow center stripe 149D at base changes to 11B at tip, stripe is 5 cm. wide at center tapering towards tips with margins 136B.

*Mature leaf color* (*upper surface*).—Yellow center stripe 12D, stripe is 4.5 cm. wide at middle tapering towards tips with margins 135A.

Flower:

*Inflorescence arrangement.*—Racemose.

*Quantity of flowers per inflorescence.*—38.

*Inflorescence dimensions.*—160 cm. in height and 28 cm. in width.

*Flower type.*—Panicle.

*Natural flowering season.*—Spring.

*Fragrance.*—None.

Fruit/seed production: None observed.

Disease and pest resistance: Resistance to diseases and pests has not been observed.

The invention claimed is:

1. A new and distinct variety of *Beschorneria* plant named 'BESYS' as described and illustrated.

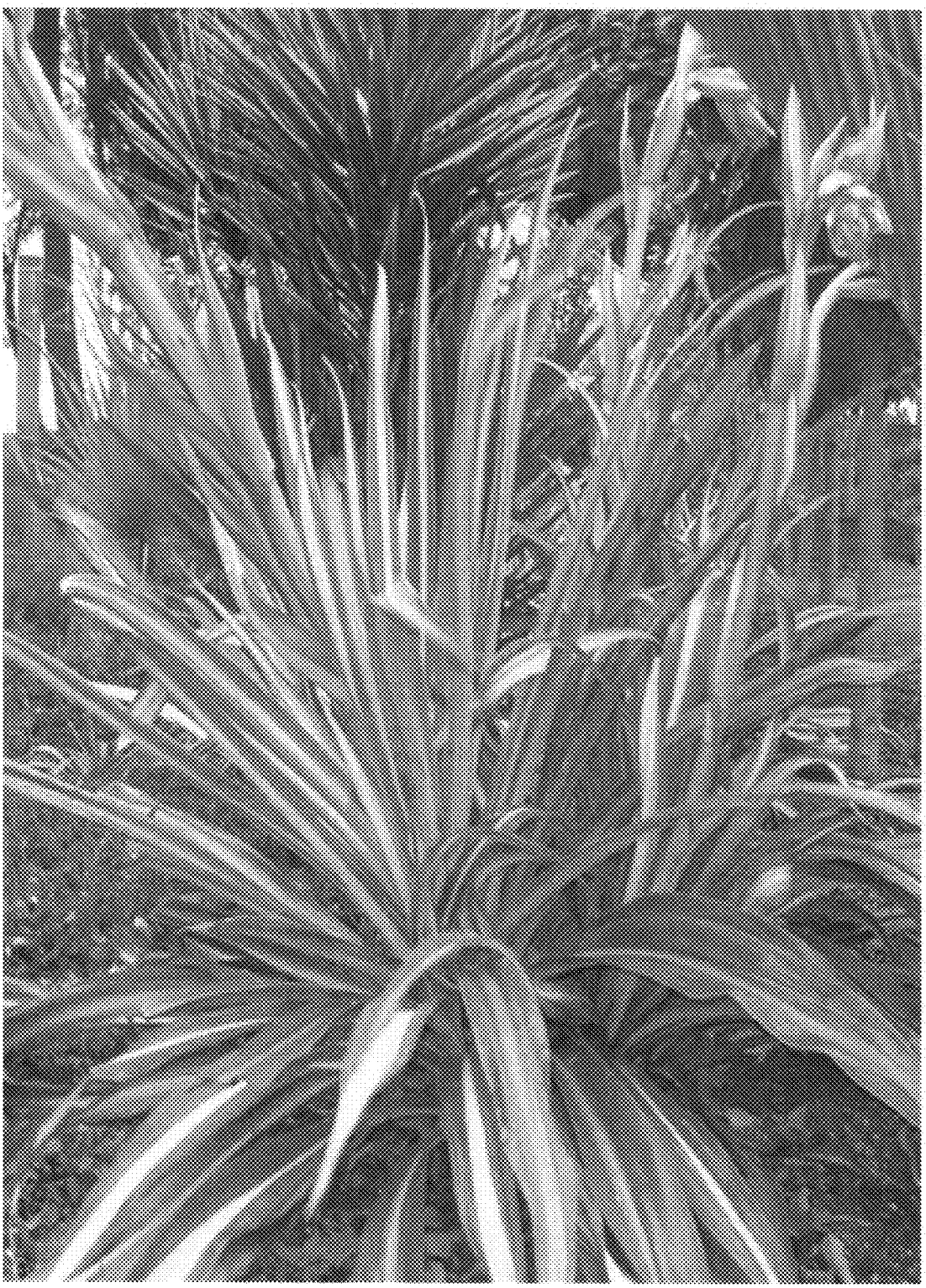

* * * * *